(12) United States Patent
Ebersole et al.

(10) Patent No.: US 7,359,060 B2
(45) Date of Patent: Apr. 15, 2008

(54) MULTI-MODE SAMPLING PROBES

(75) Inventors: Matthew D. Ebersole, Sun Prairie, WI (US); Carla S. Draper, Madison, WI (US); Jeffrey Hirsch, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 183 days.

(21) Appl. No.: 11/268,977

(22) Filed: Nov. 7, 2005

(65) Prior Publication Data

US 2007/0103690 A1    May 10, 2007

(51) Int. Cl.
G01B 9/02 (2006.01)
G01J 3/45 (2006.01)

(52) U.S. Cl. ...................... 356/477; 356/451
(58) Field of Classification Search ................ 356/436, 356/441, 442, 451, 477, 479, 501
See application file for complete search history.

(56) References Cited

U.S. PATENT DOCUMENTS

| | | |
|---|---|---|
| 5,418,615 A | 5/1995 | Doyle |
| 5,436,454 A | 7/1995 | Bornstein et al. |
| 5,585,634 A * | 12/1996 | Stevenson et al. ..... 250/339.11 |
| 5,618,615 A * | 4/1997 | Inoue et al. ............. 428/315.5 |
| 6,137,108 A * | 10/2000 | DeThomas et al. .... 250/339.07 |

* cited by examiner

*Primary Examiner*—Michael A. Lyons
(74) *Attorney, Agent, or Firm*—DeWitt Ross & Stevens; Michael C. Staggs

(57) ABSTRACT

An optical probe for use in infrared, near infrared, Raman, and other spectrometers includes a probe outer surface with a cavity defined therein. The probe emits light into a sample via emission locations on the probe outer surface, at least one being in the cavity. The light emitted into the sample is then collected at collection locations which include at least two of (a) a reflectance collection location situated on the probe outer surface for collecting diffusely reflected light from any adjacent sample; (b) a transmittance collection location situated in the cavity and receiving light transmitted across the cavity from an emission location situated on an opposite side of the cavity; and (c) a transflectance collection location situated in the cavity and receiving transflected light emitted from an emission location in the cavity, with such light being reflected from a side of the cavity opposite the transflectance collection location.

20 Claims, 2 Drawing Sheets

MULTI-MODE SAMPLING PROBES

FIELD OF THE INVENTION

This document concerns an invention relating generally to spectrometric probes, and more specifically to optical probes used for spectrometric analysis of fluid sample media (i.e., gases, liquids, powders and other flowable solids, or mixtures of these media).

BACKGROUND OF THE INVENTION

Spectrometry is a well-known technique used to identify the characteristics of gas, liquid, and solid samples, wherein light is directed at a sample and the light reflected from or transmitted through the sample is then analyzed for changes in wavelength. These changes provide information regarding the composition of the sample, its chemical bonds, and other features. Many spectrometers have a sample chamber which is located in a fixed location, with emitted light being directed into the chamber and exiting light being collected by an adjacent detector. However, such an arrangement can be inconvenient owing to the need to load the sample chamber prior to analysis of the sample, and thus spectrometers have been developed which allow "remote" sampling: a mobile probe is provided which can be situated within or adjacent to a sample of interest, with the probe emitting and collecting the light for analysis. Such an arrangement is exemplified by the SABIR probe provided with the ANTARIS spectrometer (Thermo Electron LLC, Madison, Wis., USA), which is schematically illustrated in the simplified diagram of FIG. 1. A spectrometer 100 includes an interferometer 102 emitting light at some specified wavelength(s), and this light is received by a fiberoptic cable 104 and transmitted to a gun-like probe 106, at which the light is emitted from an emission location 108 at the tip of the probe 106 onto a sample. The light is then picked up at a collection location 110 after being diffusely reflected from the sample (i.e., the light penetrates the sample to some degree before being reflected outwardly), and is transmitted back to the spectrometer 100 via a return fiberoptic cable 112 to be received at a photosensitive detector 114. The readings from the detector 114 are then processed to provide information regarding the properties of the sample. This diffuse reflectance mode of measurement is commonly used for solid samples, which tend to exhibit higher degrees of diffuse reflectance.

However, measurements of diffusely reflected (scattered) light from a sample may sometimes be weak, which can lead to difficulties in accurate sample analysis. It may then be desirable to measure light transmitted through the sample. In this case, a mirror may be situated within the sample, or on a side of the sample opposite the probe 106, so that the light from the emission location 108 passes through the sample, is reflected back through the sample from the mirror, and is then picked up at the collection location 110. This mode of measurement, known as transflectance, is commonly used for liquid and gas samples which exhibit low diffuse reflectance. Another mode of measurement, known as transmittance, modifies the probe 106 so that the collection location 110 is located opposite the emission location 108 with a space therebetween into which the sample may be received. The light then passes through the sample directly from the emission location 108 to the collection location 110.

In some cases, it may be desirable to analyze a sample using more than one of the foregoing reflectance, transmittance, and/or transflectance modes. This generally requires that the probe 106 be reconfigured or replaced so that the desired modes may be sequentially implemented on the sample, and such reconfiguration/replacement can be time-consuming and inconvenient.

SUMMARY OF THE INVENTION

The invention involves spectrometric devices and methods which are intended to at least partially solve the aforementioned problems. To give the reader a basic understanding of some of the advantageous features of the invention, following is a brief summary of preferred versions of the invention, with reference being made to the accompanying drawings to further assist the reader's comprehension. Since this is merely a summary, it should be understood that more details regarding the preferred versions may be found in the Detailed Description set forth later in this document. The claims set forth at the end of this document then define the various versions of the invention in which exclusive rights are secured.

A spectrometric probe (as exemplified by the probes 200 and 300 of FIGS. 2 and 3) includes a probe outer surface 202/302 with at least one cavity 204/304 defined therein. Light input paths 206/306 (e.g., fiberoptic cables or other light pipes) extend within or on the probe 200/300 to one or more emission locations 208/308 provided on the probe outer surface 202/302 for emitting light, wherein at least one of the emission locations 208/308 is in the cavity 204/304. Collection locations, shown at 210 and 212 in FIG. 2 and 310 and 314 in FIG. 3, are also provided on the probe outer surface 202/302. Each collection location collects light from one of the emission locations 208/308 and transmits the collected light through a corresponding light output path 216/316 (e.g., a fiberoptic cable or other light pipe(s)) extending within or on the probe 200/300. These collection locations include at least two of the following:

(1) a reflectance collection location 210/310 situated on the probe outer surface 202/302 (preferably outside the cavity 204/304) and collecting light emitted by one of the emission locations 208/308, wherein this reflectance collection location 210/310 is not located opposite either an emission location 208/308 or a reflective area defined on the probe outer surface 202/302 (i.e., the reflectance collection location 210/310 collects light which was not emitted or reflected from any side of the cavity 204/304 opposite the emission location 208/308 from which the light was emitted). The reflectance collection location 210/310 therefore receives and collects diffusely reflected light from any sample medium located adjacent the reflectance collection location 210/310;

(2) as exemplified by the probe 200, a transmittance collection location 212 situated in the cavity 204 and receiving transmitted light emitted from the cavity 204 from one of the emission locations 208 (this emission location 208 being situated on an opposite side of the cavity 204 from the transmittance collection location); and (3) as exemplified by the probe 300, a transflectance collection location 314 situated in the cavity 304 and receiving transflected light emitted from the cavity 304 from one of the emission locations 308 after such light is reflected from a side of the cavity 304 opposite the transflectance collection location 314 (with this side of the cavity 304 bearing a mirror or other reflective surface 318).

Preferably, each of the collection locations 210 and 212 (or 310 and 314) is isolated to receive light only from its coupled emission location 208/308 such that crosstalk between the reflectance, transmittance, and/or transflectance collection locations is minimized or avoided (i.e., so that each of the collection locations collects only one of transmitted, transflected, and reflected light). Crosstalk can also be reduced or avoided by having each of the coupled emission and collection locations emit and collect light over distinct wavelength ranges. For example, different emission locations 208/308 may be supplied by light sources which emit at different mean wavelengths, and/or different emission and collection locations may be equipped with filtering features (e.g., by having the light pipes or other light input/output paths 206/306 and/or 216/316 pass desired wavelengths and block others).

The probe 200/300 can therefore be inserted into a fluid sample medium so that the fluid sample medium flows into the cavity 204/304, and about the emission locations 208/308 and the collection locations 210 and 212 (or 310 and 314). When light is emitted from the emission locations 208/308 and collected from the corresponding collection locations, simultaneous (or sequential) measurement of at least two of transmittance, transflectance, and/or reflectance can be obtained from the same probe 200/300. As will be discussed below with respect to FIGS. 4-6, the foregoing arrangement can be presented in a variety of different forms. To illustrate, FIG. 5 presents a probe 500 including a reflectance collection location 510, a transmittance collection location 512, and a transflectance collection location 514, rather than only including two of these features.

Further details regarding these exemplary versions of the invention (and others) are provided in the following discussion.

DETAILED DESCRIPTION OF PREFERRED VERSIONS OF THE INVENTION

Figure 1:
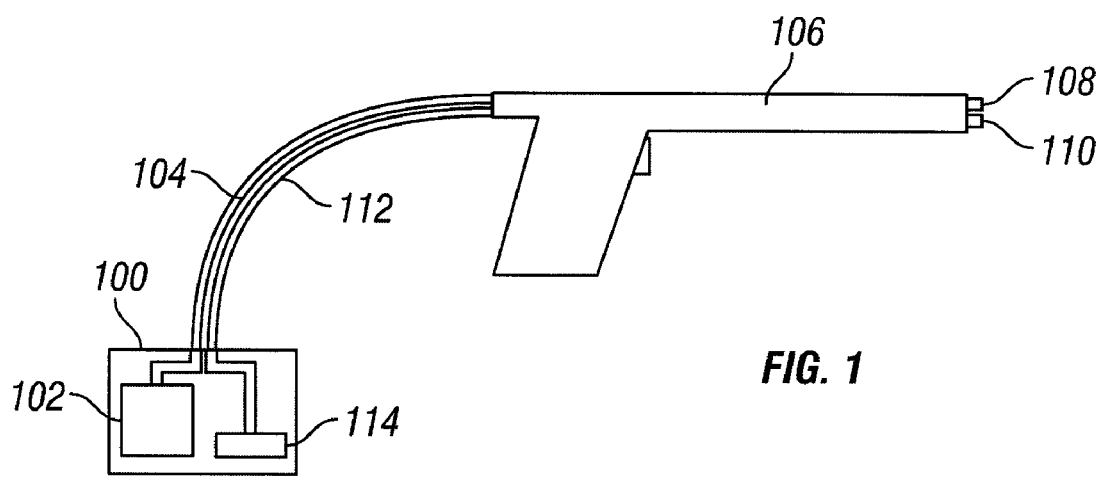
FIG. 1 is a simplified schematic diagram of a spectrometer 100 having a probe 106 extending from the spectrometer 100 by a flexible lead 104/112 whereby the probe 106 may analyze samples remote from (i.e., spaced from) the spectrometer 100.

Since several exemplary versions of the invention have already been described above, the following discussion will focus on other exemplary versions, and will also review features which were not discussed above or which would benefit from further discussion. The following discussion will often focus on features of the probe 200, but this is merely for the sake of reference, and it should be understood that discussions of the features of the probe 200 can be generally extended to other probes exemplifying the invention.

To expand on the discussion above, the light input paths 206 receive light from an interferometer (not shown) or other suitable light source, and extend within the probe 200 or along its probe outer surface 202 to emit light from the emission locations 208. One of the emission locations 208—the one depicted on the tip of the probe 200—emits light into an adjacent sample. The emitted light is scattered through the sample, as schematically depicted by the cluster of arrows adjacent the tip of the probe 200. Some of the scattered light then returns to the reflectance collection location 210, which is preferably located closely adjacent the emission location 108 on the probe outer surface 202. The light is then carried by the corresponding light output path 216 to a photosensitive detector (not shown) for measurement and analysis, as in the spectrometer 100.

At the emission location 208 located within the cavity 204, the emitted light traverses the cavity 204 (and is transmitted through the sample) for collection at the transmittance collection location 212, and for subsequent return to a detector via its light output path 216. If measurements are to be simultaneously taken from the collection locations 210 and 212, the light output paths 216 from each might supply their collected light to independent detectors, whereas if measurements are taken sequentially from the collection locations 210 and 212, their light output paths 216 may share a detector, with each collection location 210 and 212 illuminating the detector in turn.

As previously discussed, each of the light input paths 206 may be supplied with light from different light sources which provide light over different wavelength ranges. Alternatively, if different wavelength ranges are desired for different light input paths 206, all paths 206 might be supplied from the same light source, with filters provided prior to (or integrally within) the light input paths 206 so that different wavelength ranges are ultimately emitted from the emission locations 208. In other cases, it may be desirable to supply all (or at least some) of the light input paths 206 from the same light source so that the emitted light from all emission locations 208 is substantially the same (i.e., light of at least substantially the same intensity and wavelength is emitted from all emission locations 208). It can be difficult to supply identical light to multiple light input paths 206 since an interferometer or other light source may not have uniform light flux (it may project an image onto the light input paths which varies over its area). For example, where an incandescent filament is used as the ultimate light source, a light input path 206 located closer to the tip of the filament may receive different light than a light path 206 picking up light from a more distant section of the filament. In this situation, it can be useful to form the light input paths 206 of bundled fiberoptic cables or other light pipes, and at their input ends (where they receive the image of the light source), evenly distribute each of the fibers (or other elements) of the bundles about the light source. In this manner, while each of the fibers or other elements of the light input paths 206 may individually pass different light, each light input path 206 passes on average the same light (i.e., light of substantially the same net intensity and wavelength range).

Figure 2:
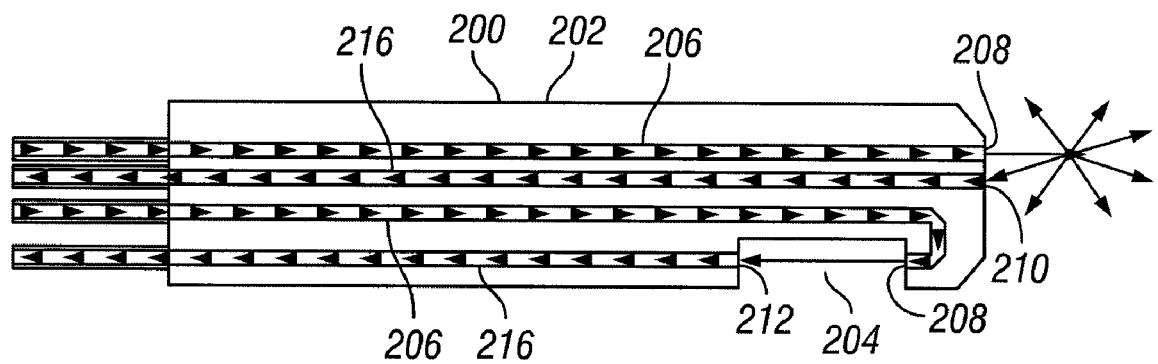
FIG. 2 is a simplified schematic diagram of a cross-section of an exemplary probe 200 (or probe tip) for insertion into a sample, with the probe 200 having light input paths 206 for emission of light at emission locations 208, with collection of scattered (diffusely reflected) light then occurring at a reflectance collection location 210 and collection of light transmitted across the cavity 204 occurring at a transmittance collection location 212, with the collected light then being returned to a spectrometer (not shown) via light output paths 216.
Figure 3:
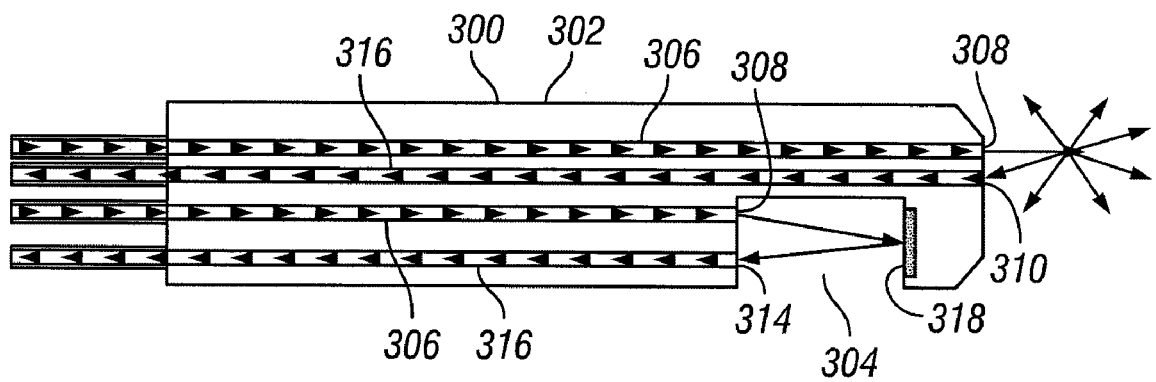
FIG. 3 is a simplified schematic diagram of a cross-section of another exemplary probe 300 (or probe tip) for insertion into a sample, with the probe 300 having light input paths 306 for emission of light at emission locations 308, with collection of scattered (diffusely reflected) light occurring at a reflectance collection location 310 and collection of transflected light across the cavity 304 occurring at a transflectance collection location 314 after reflection from a reflective surface 318, with the collected light then being returned to a spectrometer (not shown) via light output paths 316.

To briefly review the other exemplary versions of the invention depicted in the drawings, the probe 300 of FIG. 3 operates in substantially the same manner as the probe 200 of FIG. 2. However, diffusely reflected light is collected from the sample at a reflectance collection location 310, and light from the sample is additionally collected at a transflectance collection location 314. To collect light at the transflectance collection location 314, light is emitted into the cavity 304 at an emission location 308, passed through the sample across the cavity 304, reflected from a mirror or other reflective surface 318 provided on the probe outer surface 302 within the cavity 304, and is then collected at the transflectance collection location 314. Since this arrangement transmits light across the cavity 304 twice prior to collection, the light transmission path through the sample is doubled as compared to the arrangement of the probe 200 of FIG. 2.

Figure 4:
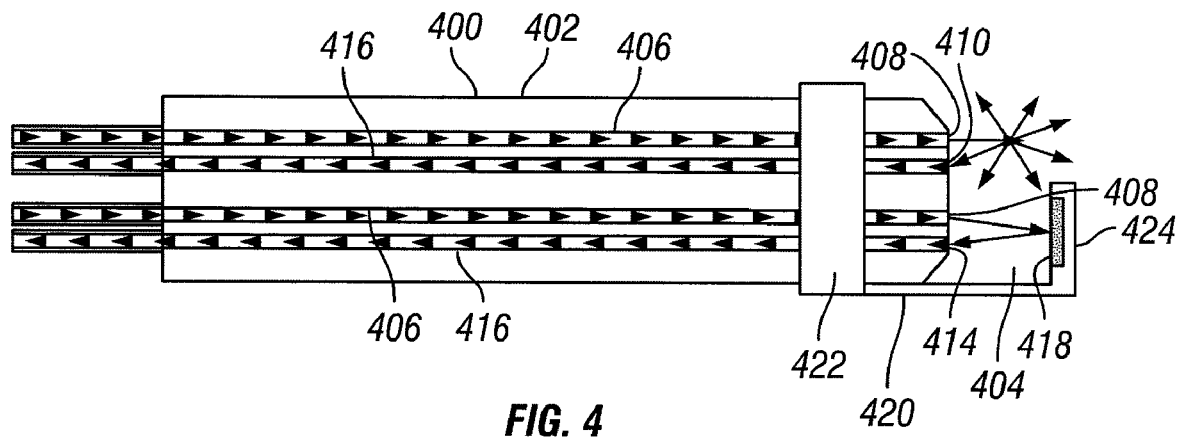
FIG. 4 is a simplified schematic diagram of a cross-section of another exemplary probe 400 (or probe tip) for insertion into a sample, with the probe 400 having light input paths 406 for emission of light at emission locations 408, with collection of scattered (diffusely reflected) light occurring at a reflectance collection location 410 and collection of transflected light occurring at a transflectance collection location 414 after reflection from a reflective surface 418 provided across the cavity 404 on a reflector mount 420 fit about the probe 400, with the collected light then being returned to a spectrometer (not shown) via light output paths 416.

Turning to FIG. 4, the probe 400 is a modified version of the probe 300 of FIG. 3. Here the cavity 404 is not defined integrally within the probe outer surface 402, but is rather provided by a reflector mount 420 affixed to define an extension of the probe outer surface 402. The cavity 404 is then situated between the reflector mount 420 and the remainder of the probe outer surface 402. The mount 420 situates a mirror or other reflective surface 418 distantly from an emission location 408 on the probe outer surface 402 so that light transmitted through a sample in the cavity 404 is reflected back to a transflectance collection location 414. The transflectance collection location 414 is situated within the cavity 404 on the probe outer surface 402 when the reflector mount 420 is present, but when the mount 420 is removed, the cavity 404 effectively disappears as well, so that the transflectance collection location 414 and its coupled emission location 408 substantially resemble the reflectance collection location 410 and its coupled emission location 408. The reflector mount 420 can have a variety of forms, with one simple preferred form having a base 422 formed as a ring which is resiliently flexible to fit about the probe outer surface 402 and then snap tightly thereon. An extension 424 then extends from the base 422 to situate the reflector 418 distantly from the transflectance collection location 414 and its coupled emission location 408.

Figure 5:
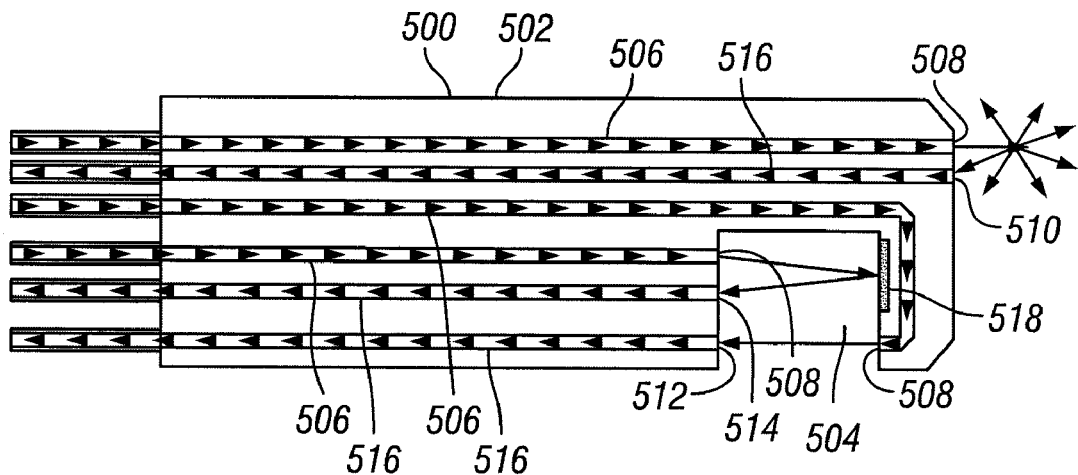
FIG. 5 is a simplified schematic diagram of a cross-section of another exemplary probe 500 (or probe tip) for insertion into a sample, with the probe 500 having light input paths 506 for emission of light at emission locations 508, with collection of scattered (diffusely reflected) light occurring at a reflectance collection location 510, collection of light transmitted across cavity 504 occurring at a transmittance collection location 512, and collection of transflected light across the cavity 504 occurring at a transflectance collection location 514 after reflection from a reflective surface 518, with the collected light then being returned to a spectrometer (not shown) via light output paths 516.

The probe 500 of FIG. 5 combines features of the probes 200 and 300 of FIGS. 2-3. The probe outer surface 502 includes a cavity 504 with a transmittance location collection 512 receiving light transmitted through the sample in the cavity 504 from an emission location 508 located on the opposite side of the cavity 504. In addition, a transflectance collection location 514 receives light originating from a coupled emission location 508 and reflected from a mirror 518 (or other reflective surface) on the side of the cavity 504 opposite the transflectance collection location 514. Finally, a reflectance collection location 510 is located on the probe outer surface 502 outside the cavity 504 to collect light diffusely reflected from the sample from an adjacent coupled emission location 508.

Figure 6:
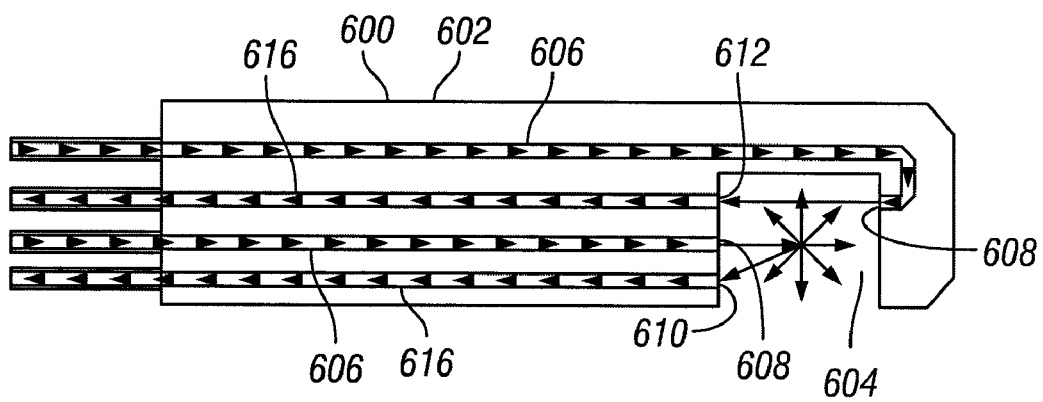
FIG. 6 is a simplified schematic diagram of a cross-section of another exemplary probe 600 (or probe tip) for insertion into a sample, with the probe 600 having light input paths 606 for emission of light at emission locations 608, with collection of scattered (diffusely reflected) light occurring at a reflectance collection location 610 within the cavity 604 and collection of light transmitted across the cavity 604 occurring at a transmittance collection location 612, with the collected light then being returned to a spectrometer (not shown) via light output paths 616.

The probe 600 of FIG. 6 can be regarded as an adaptation of the probe 200 of FIG. 2. A reflectance collection location 610 is situated within the cavity 604 to collect diffusely reflected light from within (or slightly outside) the cavity 604, with such light originating from a coupled emission location 608 which is also situated within the cavity 604. (However, this emission location 608 need not necessarily be located within the cavity 604, e.g., it could be situated on the probe outer surface 602 slightly outside the cavity 604 to direct light into the cavity 604 for receipt at the reflectance collection location 610.) A transmittance collection location 612 is also provided within the cavity 604 for receipt of light transmitted through the sample from a coupled emission location 608 situated on the opposite side of the cavity 604, in much the same manner as in the probes 200 and 500. One particular benefit of the probe 600 is that the light collected at the reflectance collection location 610 and the transmittance collection location 612 is known to relate to the same region of the sample (the portion of the sample located in the cavity 604). In contrast, readings taken from the reflectance collection location 210 and the transmittance collection location 212 of the probe 200 of FIG. 2 might have lesser correlation (e.g., if the sample's properties vary between the reflectance collection location 210 and the transmittance collection location 212).

It should be understood that while probes exemplifying the invention may be provided as wand-like members extending from a flexible lead (this lead being defined by the bundled light input and output paths) in forms substantially similar to those depicted in the drawings, the probes could assume very different configurations. As one example, probes could be gun-like (such as the probe 100 of FIG. 1), with emission and collection locations being incorporated on or about their "barrels." In any event, the tips of the probes are preferably rounded/streamlined, and are preferably formed with minimal diameter, so that the probes offer lesser resistance to insertion within powders, viscous liquids, and other thick fluids. In this respect, taking the probe 200 of FIG. 2 as an example, it can be useful if the cavity 204 is defined as a notch-like valley extending through the probe 200 from one side to an opposite side, rather than forming the cavity 204 as a pocket-like depression circumferentially bounded by the probe 200. The latter type of cavity 204 (a pocket-like cavity) can retain material from a sample and can therefore be more difficult to clean than a notch-like cavity. While the cavity 204 is preferably integrally defined within the outer surface 202 of the probe 200, as discussed above in reference to the probe 400 of FIG. 4, the cavity 204 could instead be defined within the probe outer surface 202 via the addition of an extension to the probe outer surface 202 (such as the extension 420 of the probe 400 of FIG. 4), whereby the cavity 204 is defined between the extension and the remainder of the probe outer surface 202.

Additionally, the emission locations and collection locations can assume a variety of different locations and configurations. As an example, while the reflectance-collection locations 210, 310, 410, and 510 are illustrated on the distal tips of their respective probes, they could instead be provided on the sides of the probes, or as depicted in the probe 600 of FIG. 6, they could be provided in the cavity 504 on the probe outer surface 502.

As another exemplary modification, where multiple collection locations are all located within the interior of a cavity (as with the transmittance and transreflectance collection locations 512 and 514 of the probe 500, and as with the reflectance and transmittance collection locations 610 and 612 of the probe 600), these collection locations could be spaced circumferentially within their probes rather than radially (i.e., rather than being staggered depthwise within their cavities, as depicted in FIGS. 5 and 6).

Furthermore, while the foregoing probes are depicted with each collection location being coupled to a single emission location, multiple emission locations could instead be coupled to fewer collection locations (or conversely, multiple collection locations could be coupled to fewer emission locations). For example, in the probe 200, the reflectance collection location 210 could be provided by the terminal ends of several light input paths 206 (e.g., fiberoptic cables or other light pipes) which surround or are otherwise situated about the terminal ends of one or more light output paths 216 (again fiberoptic cables or other light pipes). In this arrangement, the several light input paths 206 defining the reflectance collection location 210 collect scattered light originating from the light output paths 216. As another example, the emission and collection locations of the probe 600 might be altered such that the emission location 608 within the cavity 604 transmits light across the cavity 204 to be received by a transmittance collection location (one not depicted in FIG. 6), and at the same time an adjacent reflectance collection location 210 (as depicted in FIG. 6) can collect scattered light originally emitted by the same emission location 608.

It is also possible that any of the foregoing probes might include additional reflectance, transmittance, and/or transflectance collection locations operating in parallel to those already provided. For example, the probe 200 might include an additional coupled set of an emission location 208 and a reflectance collection location 210 on the tip or side of the probe outer surface 202, and/or the probe 200 might include an additional coupled set of an emission location 208 and a transmittance collection location 212 located in the same cavity 204 (or in a second cavity 204 defined on the probe outer surface 202). These collection locations could be redundant in that they may be intended to replicate measurements from other collection locations for purpose of error-checking. Alternatively, the different collection locations might instead be intended to collect qualitatively different measurements, as by having different collection locations adapted to collect light over different wavelength ranges. For example, their coupled emission locations might emit light over different wavelength ranges, and/or the collection locations might be equipped with filters such that the different collection locations only collect wavelengths falling within certain ranges.

The light input and output paths preferably (but need not) take the form of fiberoptic cables, and they could instead take the form of other light-transmitting media, e.g., gel tubes, hollow tubes with internally reflecting surfaces, translucent films or other translucent members, or other matter which directs light along the desired path (preferably with high internal reflection such that minimal light loss occurs). Fiberoptic cables, being readily available and relatively inexpensive, are merely the presently preferred form of the input and output paths. Further, the input and output paths need not be continuous, and may include different media along their lengths. For example, an input path could include adjacent sections formed of single fibers, bundled fibers, films, or other translucent media, with different sections either being transparent to selected wavelength ranges or including filtering features (such as blocking of selected wavelengths).

It should be understood that preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A spectrometric method comprising:
   a. inserting a probe within a fluid sample medium, the probe having a probe outer surface including a cavity, wherein the fluid sample medium flows into the cavity when the probe is inserted into the fluid sample medium;
   b. emitting light from the probe at two or more emission locations, wherein at least a portion of the emitted light is emitted into the cavity, and each of the emission locations emits light having a different mean wavelength;
   c. collecting light from at least two collection locations on the probe outer surface, the collected light including at least two of the following types:
      (1) light transmitted through the fluid sample medium, the transmitted light being emitted from an emission location at one side of the cavity and collected from a collection location at an opposing side of the cavity;
      (2) light transflected through the fluid sample medium, the transflected light being emitted from an emission location at one side of the cavity and reflected from an opposite side of the cavity; and
      (3) reflected light from the fluid sample medium, the reflected light not being emitted or reflected from any side of the cavity opposite any location from which the reflected light was originally emitted.

2. The spectrometric method of claim 1 wherein each of the collection locations collects only one of the types of light.

3. The spectrometric method of claim 1 wherein light is simultaneously collected from the collection locations.

4. The spectrometric method of claim 1 wherein the emitted light is provided by an interferometer.

5. The spectrometric method of claim 1 wherein:
   a. the light is emitted from the probe at two or more emission locations;

b. the probe further comprises:
  (1) two or more light input paths, each extending through the probe to one of the emission locations;
  (2) an interferometer supplying light to the light input paths.
6. The spectrometric method of claim 1:
a. further comprising two or more light output paths, each extending through the probe from one of the collection locations, and
b. wherein each of the light output paths attenuates light over a different wavelength range.
7. A spectrometric probe comprising:
a. a probe outer surface, the probe outer surface including a cavity defined therein;
b. two or more emission locations on the probe outer surface from which light is emitted, wherein at least one of the emission locations is in the cavity, wherein each of the emission locations emits light having a different mean wavelength;
c. collection locations on the probe outer surface, each collection location collecting light from one of the emission locations, wherein:
  (1) at least one of the collection locations collects light emitted from the cavity, and
  (2) the collection locations include at least two of:
    (a) a transmittance collection location situated in the cavity and receiving transmitted light from one of the emission locations, this emission location being situated on an opposite side of the cavity;
    (b) a transflectance collection location situated in the cavity and receiving transflected light from one of the emission locations after such light is reflected from a side of the cavity opposite the collection location;
    (c) a reflectance collection location situated on the probe outer surface and receiving reflected light from one of the emission locations, wherein the reflected light is not emitted or reflected from any side of the cavity opposite the emission location from which the reflected light was emitted.
8. The spectrometric probe of claim 7 wherein each of the collection locations collects only one of transmitted, transflected, and reflected light.
9. The spectrometric probe of claim 7 further comprising photosensitive detectors, each detector receiving light from one of the collection locations, wherein the detectors are simultaneously active to detect light from the collection locations.
10. The spectrometric probe of claim 7 further comprising:
a. an interferometer, and
b. one or more light input paths extending from the interferometer to the emission locations,
wherein the interferometer provides the light into the light input paths to be emitted by the emission locations.
11. The spectrometric probe of claim 7:
a. wherein:
  (1) two or more emission locations are provided on the probe outer surface, and
  (2) each emission location has a light input path extending therefrom through the probe; and
b. further comprising an interferometer providing light to the light input paths.
12. The spectrometric probe of claim 7:
a. further comprising two or more light output paths, each extending through the probe from one of the collection locations, and b. wherein the light output paths pass different wavelength ranges of light.
13. A spectrometric probe having a probe outer surface including a cavity defined therein, and comprising:
a. two or more light input paths extending through the probe, wherein:
  (1) each light input path extends to an emission location on the probe outer surface, with each emission location emitting light from its light input path, wherein each of the emission locations emits light having a different mean wavelength, and
  (2) at least one of the emission locations emits light into the cavity from its light input path;
b. a first light output path extending through the probe from a first collection location on the probe outer surface, wherein the first collection location:
  (1) is not located opposite either:
    (a) an emission location, or
    (b) a reflective area defined on the probe outer surface, to receive light therefrom, and
  (2) collects light first emitted by one of the emission locations and then diffusely reflected from any sample medium located adjacent the first collection location; and
c. a second light output path extending through the probe from a second collection location on the cavity, wherein the second collection location collects light emitted into the cavity from one of the emission locations.
14. The spectrometric probe of claim 13 wherein:
a. the first collection location collects light first emitted by a first emission location and then diffusely reflected from any sample medium located adjacent the first collection location, and
b. the first collection location is located immediately adjacent the first emission location on the probe outer surface.
15. The spectrometric probe of claim 14 wherein both the first emission location and the first collection location are situated outside the cavity on the probe outer surface.
16. The spectrometric probe of claim 13 wherein the second collection location collects light emitted into the cavity from a second emission location located in the cavity opposite the second collection location, whereby the second collection location collects light transmitted through any sample medium located in the cavity.
17. The spectrometric probe of claim 13:
a. further comprising a reflective surface defined on the cavity opposite the second collection location; and
b. wherein the second collection location collects light emitted into the cavity from a second emission location located in the cavity adjacent the second collection location, whereby the second collection location collects light transflected through any sample medium located in the cavity.
18. The spectrometric probe of claim 13 further comprising an interferometer supplying light to the light input paths.
19. The spectrometric probe of claim 13 wherein the first and second light output paths pass different wavelength ranges of light.
20. A spectrometric method comprising:
a. inserting a probe within a fluid sample medium, the probe having a probe outer surface including a cavity, wherein the fluid sample medium flows into the cavity when the probe is inserted into the fluid sample medium;

b. emitting light from the probe at one or more emission locations, wherein at least a portion of the emitted light is emitted into the cavity;
c. simultaneously collecting light from at least two collection locations on the probe outer surface, the collected light including at least two of the following types:
  (1) light transmitted through the fluid sample medium, the transmitted light being emitted from an emission location at one side of the cavity and collected from a collection location at an opposing side of the cavity;
  (2) light transfiected through the fluid sample medium, the transfiected light being emitted from an emission location at one side of the cavity and reflected from an opposite side of the cavity; and
  (3) reflected light from the fluid sample medium, the reflected light not being emitted or reflected from any side of the cavity opposite any location from which the reflected light was originally emitted.

* * * * *